(12) United States Patent
Argus et al.

(10) Patent No.: US 6,344,185 B1
(45) Date of Patent: Feb. 5, 2002

(54) SELF-TANNING COMPOSITION

(75) Inventors: Lisa Argus, West Haven; Tetsuya Kambe, Darien, both of CT (US)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/491,854

(22) Filed: Jan. 26, 2000

Related U.S. Application Data

(60) Provisional application No. 60/117,698, filed on Jan. 29, 1999.

(51) Int. Cl.$^7$ .................................................. A61K 7/42

(52) U.S. Cl. .......................... 424/59; 424/60; 424/400; 424/401

(58) Field of Search ............................ 424/59, 60, 400, 424/401

(56) References Cited

U.S. PATENT DOCUMENTS 5,700,452 A * 12/1997 Deckner et al. .............. 424/59

* cited by examiner

*Primary Examiner*—Jose' G. Dees
*Assistant Examiner*—Michael A. Williamson
(74) *Attorney, Agent, or Firm*—Melvin I. Stoltz

(57) ABSTRACT

By combining dihydroxyacetone as the active skin coloring agent in combination found with a blend of dispersion polymers and polyester polymers, an easily employed, self-tanning formulation is realized which produces a long lasting, naturally appearing coloring of the skin without any orange pigmentation being produced. In addition, tan colored skin produced by the present invention maintains the desired color for extended periods of time. In the present invention, the dispersion polymers stabilize the dihydroxyacetone as well as provide a thickening agent for the composition. In addition, the present invention also incorporates an oil soluble polyester polymer in combination with the other ingredients which achieves a formulation which provides a slow release of the active ingredient.

7 Claims, No Drawings

SELF-TANNING COMPOSITION

RELATED APPLICATIONS

This application relates to U.S. Provisional Patent Application Serial No. 60/117,698, filed Jan. 29, 1999 for a Self-Tanning Composition.

TECHNICAL FIELD

This invention relates to tanning compositions and, more particularly, to self-tanning compositions having improved, longer lasting results.

BACKGROUND ART

Tanning or coloring of an individual's skin surface has long been fashionable and believed to impart to the individual a pleasing or desirable appearance. However, in more recent years, evidence has been uncovered which has proven that a natural tanning caused by ultraviolet radiation of the sun causes substantial damage to the skin. In particular, it has been demonstrated that prolonged exposure to the sun's ultraviolet rays substantially increased the risk of melanoma or skin cancer. Consequently, many individuals have avoided direct sunlight to impart a tan or coloring to the skin.

In view of the conflict between many individual's desire for a tan or bronzed colored skin surface and the desire to avoid ultraviolet radiation, self-tanning or sun-less tanning compositions have become increasingly popular. Typically, these self-tanning or sun-less tanning compositions incorporate dihydroxyacetone as the active ingredient.

These prior art formulations incorporating dihydroxyacetone are capable of providing coloring to the skin without exposing the skin to the damaging effects of ultraviolet light. However, although coloring of the skin is achieved, difficulty has been encountered in controlling the color to the precisely desired shade as well as eliminating a commonly produced orange color, typically caused from skin exposure to dihydroxyacetone. In addition, the coloring effect is not long lasting, thereby requiring repeated treatment to maintain the tanned skin appearance.

Therefore, it is a principal object of the present invention to provide a self-tanning lotion which produces a naturally appearing skin tone while virtually eliminating the production of any orange coloring.

Another object of the present invention is to provide a self-tanning lotion having the characteristic features described above which provides a long lasting, tanned skin appearance.

Another object of the present invention is to provide a self-tanning lotion having the characteristic features described above which is easily employed by a user and easily spread on the skin surface in a uniform, consistent manner.

Other and more specific objects will in part be obvious and will in part appear hereinafter.

DETAILED DESCRIPTION

By employing the present invention, all of the difficulties and drawbacks found with prior art formulations have been eliminated, and an easily employed, self-tanning formulation is realized which produces a long lasting, naturally appearing coloring of the skin without any orange pigmentation being produced. In addition, tan colored skin produced by the present invention maintains the desired color for extended periods of time. This unique result is obtained by combining dihydroxyacetone as the active ingredient with a blend of dispersion polymers and polyester polymers. By employing this formulation, a unique, efficient, and highly desirable self-tanning composition is attained.

As is well known, skin is divided into three layers: the epidermis, the dermis, and the subcutaneous tissue. The outer layer of the skin is called the epidermis, and varies in thickness from about 0.3 mm to 1.5 mm. The outermost layer of the epidermis is the stratum corneum (horny layer), which is comprised of keratinized cells. The thickness of the stratum corneum varies greatly on different parts of the body.

The bottommost layer of the epidermis, called the basal cell layer, rests upon the basement membrane separating the epidermis from the dermis. The basal cells are the only epidermal cells that proliferate. The basal cells proliferate and, by cell division, form the keratinocytes. The keratinocytes synthesize insoluble protein which remains in the cells and will eventually become a major component of the outer layer (the stratum corneum horny layer). The keratinocytes continue to divide and to migrate from the bottommost layer to the outermost layer, until the cells finally die. In this process of keratinization, the cells continue to flatten until they finally die as they reach the surface to form the stratum corneum (horny layer) and are sloughed off.

In the present invention, the dispersion polymers stabilize the dihydroxyacetone as well as provide a thickening agent for the composition. In this way, the active ingredient is more easily applied to the skin surface and uniformly spread thereon for absorption therein.

In addition, the present invention also incorporates an oil soluble polyester polymer in combination with the other ingredients which achieves a formulation which provides a slow release of the active ingredient into the stratum corneum which enables the color to develop over a longer period of time. As a result, a longer lasting, more natural looking tan is realized.

In accordance with the present invention, it has been found that the active ingredient, dihydroxyacetone, preferably comprises between about 2% and 8% by weight based upon the weight of the entire composition in order to obtain the desired self tanning or sun-less tanning effect. In addition, a liquid dispersion polymer is incorporated with the active ingredient in order to thicken the composition and enable the product to be spread more evenly on the skin. Preferably, the quantity employed for the liquid dispersion polymer ranges between about 1% and 2.5% by weight based upon the weight of the entire composition.

In accordance with the present invention, the preferred liquid dispersion polymer incorporated into the sun-less tanning composition of the present invention comprises the homopolymer, dimethylaminoethylmethacrylate dispersed in propylene glycol dicaprylate/dicaprate with polyquaternium -37 and PPG-1 trideceth-6. In this regard, it has been found that the preferred liquid dispersion polymer employed comprises Salcare SC-96, manufactured by Ciba Specialty Chemical Corp. Of High Point, N.C. Although other liquid dispersion polymers comprising the ingredients detailed above may be employed with equal efficacy, Salcare SC-96 has been found to provide the desired results when intermixed with the other components of this invention.

In completing the principal ingredients for the sun-less tanning formulation of the present invention, an oil soluble polyester polymer is employed which synergistically interacts with the other principal ingredients, providing a longer lasting, time released dispersion of the active ingredient into the stratum corneum of the skin. In order to attain the desired results, it has been found that trimethylpentanediol/adipic acid/isononanoic acid copolymer provides the desired result. In addition, it has also been found that between about 1% and 5% by weight of the weight of the entire composition of the oil soluble polyester polymer is employed in order to achieve the desired interaction thereof with the other ingredients.

In achieving the advantageous results of the present invention, the preferred oil soluble polyester polymer employed comprises Lexorez TC-8, manufactured by Inolex of Philadelphia, Pa. Although any alternate oil soluble polyester polymer having the components described above can be employed, this particular product has been found to be most efficacious in achieving the desired results.

The final ingredient incorporated into the sun-less tanning formulation of the present invention comprises water, preferably deionized water, which is employed in a sufficient quantity to bring the composition to 100 percent. In Table 1, the preferred overall formulations of this invention are detailed. In addition, TABLE II is also provided wherein the preferred formulations of the present invention are provided with each ingredient identified by its generic name or CTFA designation.

TABLE I

Self-Tanning Composition

| Ingredient | Quantity (% by Wgt.) |
| --- | --- |
| Active Tanning Agent | 2–8 |
| Thickener/Stabilizer | 1–2.50 |
| Polymer | 1–5 |
| Water | q.s. to 100% |

TABLE II

Preferred Self-Tanning Composition

| Ingredient | Quantity (% by Wgt.) |
| --- | --- |
| Dihydroxyacetone | 2.00–8.00 |
| Polyquaternium 37/Propylene Glycol Dicaprylate/Dicaprate/PPG-1 Trideceth-6 | 1.00–2.50 |
| Trimethylpentanediol/Adipic Acid/Isononanoic Acid Copolymer | 1.00–5.00 |
| Water | q.s. to 100% |

In addition to employing the ingredients and formulations detailed above and fully described in Tables I and II, the self-tanning compositions of the present invention may also incorporate additional ingredients and additives. Preferably, these additional additives comprise one or more selected from the group consisting of the emollients, humectants, emulsifiers, preservatives, and chelating agents.

In the preferred embodiment, one or more emollients are employed and are selected from the group consisting of myristyl myristate and octyl palmitate. The preferred emulsifier employed in the formulation of the present invention comprises one or more selected from the group consisting of steareth-2, steareth-21, and cetearyl alcohol.

Preservatives are also preferably employed and comprise one or more selected from the group consisting of diazolidinyl urea, methylparaben, and propylparaben. Finally, it is also preferred to employ glycerin as a humectant and disodium EDTA as a chelating agent.

In Table III, the preferred formulation of the self-tanning composition of the present invention is detailed, with each of the preferred ingredients provided with the preferred quantities thereof. In this composition, each of the ingredients are defined with the preferred quantity detailed therein as the weight percent of each ingredient, based upon the weight of the entire formulation.

TABLE III

Preferred Self-Tanning Lotion Formulation

| Ingredients (CTFA Designation) | Trade Name | Quanity (% by Wgt.) |
| --- | --- | --- |
| Dihydroxyacetone | DHA | 3.00 |
| Myristyl Myristate | Ceraphyl 424 | 3.50 |
| Glycerin | Glycerin | 3.00 |
| Steareth-2 | Brij-72 | 2.75 |
| Octyl Palmitate | Pelemol OP | 2.00 |
| Polyquaternium-37/Propylene Glycol Dicaprylate/Dicaprate/PPG-1 Trideceth-6 | Salcare SC-96 | 1.50 |
| Trimethylpentanediol/Adipic Acid/Isononanoic Acid Copolymer | Lexorez TC-8 | 1.00 |
| Steareth-21 | Brij-721 | 0.80 |
| Cetearyl Alcohol | TA-1618 | 0.80 |
| Diazolidinyl Urea | Germall II | 0.30 |
| Methylparaben | Methylparaben | 0.15 |
| Propylparaben | Propylparaben | 0.05 |
| Disodium EDTA | Disodium EDTA | 0.05 |
| Water | Deionized Water | q.s. to 100% |

In addition to the ingredients detailed in Table III, the preferred formulation of the self-tanning composition of the present invention may also incorporate fragrances, vitamins, oils and other similar additives. However, these further ingredients are optional and may be employed if their benefits are desired. Typically, fragrances, if employed, would range between about 0.1% and 1% by weight based upon the weight of the entire composition, while the other additives would typically range between about 0.005% and 0.1% by weight based upon the weight of the entire composition.

As is evident from the foregoing detailed disclosure, the present invention achieves an easily employed, long lasting, self-tanning composition which overcomes the difficulties and drawbacks found in prior art compositions. As detailed herein, and clearly demonstrated in the following examples, the use of a generally conventional self-tanning composition along with the incorporation of a liquid dispersion polymer capable of thickening the tanning composition and enhancing its spreadability in combination with an oil soluble polyester polymer provides substantially superior results.

BEST MODE FOR CARRYING OUT THE INVENTION

In order to substantiate the efficacy of the long-lasting, self-tanning composition of the present invention-, several tests were conducted on numerous individuals wherein the tanning differences between formulations made in accordance with the present invention were compared with similar formulations which were devoid of the unique blend of the dispersion polymers and the oil soluble polyester polymers of the present invention. However, it is to be understood that the following examples are intended as a teaching of the best mode for carrying out the present invention and examples of the efficacy of the present invention, without limiting the breath of this discovery.

In conducting the tests detailed below, two separate and independent self-tanning formulations were prepared and applied to the skin surface of several tests subjects. The formulation employed in accordance with the present invention is detailed in Table IV, and is consistent with the preferred embodiment disclosed in Table III, while also incorporating several additional additives. The control formulation also applied to the test subjects in an identical manner is detailed and Table V.

TABLE IV

| Trade Name | CTFA | Quanity (% by Wgt.) |
|---|---|---|
| Deionized Water | Water | 78.56 |
| DHA | Dihydroxyacetone | 5.00 |
| Ceraphyl 424 | Myristyl Myristate | 3.50 |
| Glycerin | Glycerin | 3.00 |
| Brij-72 | Steareth-2 | 2.75 |
| Pelemol OP | Octyl Palmitate | 2.00 |
| Salcare SC-96 | Polyquaterniium-37 Propylene Glycol Dicaprylate/ Dicaprate | 1.50 |
| Lexorez TC-8 | Trimethylpentanedio/Adipic Acid/ Isononanoic Acid Copolymer | 1.00 |
| Brij-721 | Steareth-21 | 0.80 |
| TA-1618 | Cetearyl Alcohol | 0.80 |
| Frag Ch12111 | Fragrance | 0.50 |
| Germall II | Diazolidinyl Urea | 0.30 |
| Methlparaben | Methylparaben | 0.15 |
| Propylparaben | Propylparaben | 0.05 |
| Disodium EDTA | Disodium EDTA | 0.05 |
| Macadamia Nut Oil | Macadamia Ternifolia Nut Oil | 0.01 |
| Vitamin E | Tocopheryl Acetate | 0.01 |
| Vitamin A | Retinyl Palmitate | 0.01 |
| Biodyness TRF-25% | Saccharomyces Lysate Extract Water | 0.01 |

TABLE V

| Trade Name | CTFA | Quanity (% by Wgt.) |
|---|---|---|
| Deionized Water | Water | 78.56 |
| DHA | Dihydroxyacetone | 5.00 |
| Ceraphyl 424 | Myristyl Myristate | 3.50 |
| Veegum Ultra | Magnesium Aluminum Silicate | 2.00 |
| Brij-72 | Steareth-2 | 2.75 |
| Pelemol OP | Octyl Palmitate | 2.00 |
| Brij-721 | Steareth-21 | 0.80 |
| TA-1618 | Cetearyl Alcohol | 0.80 |
| Xanthan Gum | Xanthan Gum | 0.50 |
| Frag Ch12111 | Fragrance | 0.50 |
| Germall II | Diazolidinyl Urea | 0.30 |
| Methlparaben | Methylparaben | 0.15 |
| Propylparaben | Propylparaben | 0.05 |
| Disodium EDTA | Disodium EDTA | 0.05 |
| Macadamia Nut Oil | Macadamia Ternifolia Nut Oil | 0.01 |
| Vitamin E | Tocopheryl Acetate | 0.01 |
| Vitamin A | Retinyl palmitate | 0.01 |
| Biodynes TRF-25% | Saccharomyces Lysate Extract Water | 0.01 |

EXAMPLES

In order to demonstrate the efficacy of the self-tanning composition of the present invention, numerous tests were conducted using several different subjects and applying identical amounts of the compositions detailed in Tables IV and V to separate, identicaliy shaped areas on each individual. In preparation, each test subject was asked to wash with an exfoliating shower scrub on their forearm and dry their forearm for 15 minutes. Then, two test sites or panels were identified, one as Site "A" and one as Site "B". Each site on each subject was marked on the forearm, with each site comprising a dimension of one inch by two inches.

Baseline measurements were taken of each test site or panel using a Minolta Chromameter C.R.-300. Then, 40 milligrams of the formulation defined in Table IV was applied to test panel site "A" on each subject, while the formulation defined in Table V was applied to test panel site "B" on each individual. Measurements were taken from both test sites on each test subject using the Minolta Chromameter 48 hours after application and then again at 72 hours after application. The results of these tests are shown in Table VI.

TABLE VI

| Time | | 48 Hours | | 72 Hours | |
|---|---|---|---|---|---|
| Test Subject | Test Panel | Minolta Chromameter | Visual | Minolta Chromameter | Visual |
| 1 | A | −3.62 | Darker | −2.78 | Darker |
|   | B | −2.74 | Lighter | −2.65 | Lighter |
| 2 | A | −4.66 | Darker | −2.85 | Darker |
|   | B | −3.45 | Lighter | −2.25 | Lighter |
| 3 | A | −4.92 | Darker | −3.79 | Darker |
|   | B | −4.17 | Lighter | −3.19 | Lighter |
| 4 | A | −3.88 | Darker | −1.72 | Slightly Darker |
|   | B | −3.19 | Lighter | −1.10 | Slightly Lighter |
| 5 | A | −3.08 | Darker | −2.78 | Darker |
|   | B | −2.99 | Lighter | −1.47 | Lighter |

As is evident from a review of Table VI, the formulation manufactured in accordance with the present invention which incorporates the unique combination of a liquid dispersion polymer and an oil soluble polyester polymer produced substantially superior results. As detailed in Table VI, in each instance, the area of each test subject upon which the formulation of the present invention was applied proved to be darker in color than the substantially identical formulation devoid of the unique combination of ingredients of the present invention. As a result, it was concluded that the formulation of the present invention produced tanning of skin surfaces which were substantially darker than then the control formulation and remained darker for a longer period of time.

It will thus be seen that the object set forth above, among those made apparent from the preceding description, are efficiently obtained and, since certain changes may be made in the above composition without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in the claims, ingredients or compounds recited in the singular are intended to include compatible mixtures of such ingredients wherever the sense permits.

Having described our invention, what we claim as new and desire to secure by Letters Patent is:

1. A self-tanning composition for providing long lasting, naturally appearing coloring to the skin comprising:

A. between about 2% and 8% by weight based upon the weight of the entire composition of an active skin coloring agent wherein the active skin coloring component comprises dihydroxyacetone;

B. between about 1% and 2.5% by weight based upon the weight of the entire composition of a liquid dispersion polymer capable of thickening the composition and enhancing the spreadability thereof;

C. between about 1% and 5% by weight based upon the weight of the entire composition of an oil soluble polyester polymer, said oil soluble polyester polyester polymer being defined as comprising trimethylpentanediol/adipic acid/isononanoic acid copolymer; and D. de-ionized water forming the balance.

2. The self-tanning composition defined in claim 1, wherein the liquid dispersion polymer is further defined as comprising the homopolymer, dimethylaminoethylmethacrylate dispersed in propylene glycol dicaprylate/dicaprate with polyquaternium -37 and PPG-1 trideceth-6.

3. The self-tanning composition defined in claim 2, wherein the oil soluble polyester polymer is selected for interacting with the other ingredients to provide a longer lasting, time-released dispersion of the active ingredient into the skin surface.

4. The self-tanning composition defined in claim 2, and further comprising one or more additives selected from the group consisting of emollients, humectants, emulsifiers, preservatives, chelating agents, fragrances, oils, and vitamins.

5. The self-tanning composition defined in claim 4, wherein the composition comprises one or more emollients selected from the group consisting of myristyl myristate and octyl palmitate.

6. The self-tanning composition defined in claim 4, wherein the composition comprises one or more emulsifiers selected from the group consisting of steareth-2, steareth-21, and cetearyl alcohol.

7. The self-tanning composition defined in claim 4, wherein the composition comprises one or more preservatives selected from the group consisting of diazolidinyl urea, methylparaben, and propylparaben.

* * * * *